(12) United States Patent
Bingham et al.

(10) Patent No.: US 8,785,475 B2
(45) Date of Patent: Jul. 22, 2014

(54) LIPOIC ACID DERIVATIVES

(75) Inventors: Paul Bingham, Centereach, NY (US);
Tom Kwok, Miller Place, NY (US);
Zuzana Zachar, Centereach, NY (US)

(73) Assignee: Cornerstone Pharmaceuticals, Inc., Cranbury, NJ (US)

( * ) Notice: Subject to any disclaimer, the term of this patent is extended or adjusted under 35 U.S.C. 154(b) by 860 days.

(21) Appl. No.: 12/105,096

(22) Filed: Apr. 17, 2008

(65) Prior Publication Data

US 2008/0262034 A1 Oct. 23, 2008

Related U.S. Application Data

(60) Provisional application No. 60/912,598, filed on Apr. 18, 2007.

(51) Int. Cl.

| | | |
|---|---|---|
| A61K 31/47 | (2006.01) | |
| A61K 31/185 | (2006.01) | |
| A61K 31/19 | (2006.01) | |
| A61K 31/192 | (2006.01) | |
| A61K 31/28 | (2006.01) | |
| A61K 31/295 | (2006.01) | |
| A61K 31/385 | (2006.01) | |
| A61K 31/40 | (2006.01) | |
| C07C 53/128 | (2006.01) | |
| C07C 321/00 | (2006.01) | |
| C07D 207/325 | (2006.01) | |
| C07D 215/36 | (2006.01) | |
| C07D 235/00 | (2006.01) | |
| C07D 339/08 | (2006.01) | |
| C07F 15/02 | (2006.01) | |

(52) U.S. Cl.
USPC ........... 514/312; 514/393; 514/423; 514/436; 514/502; 514/568; 546/153; 548/303.7; 548/530; 549/22; 556/144; 562/426; 562/512

(58) Field of Classification Search
None
See application file for complete search history.

(56) References Cited

U.S. PATENT DOCUMENTS

| | | | |
|---|---|---|---|
| 5,750,141 A | | 5/1998 | Roberts et al. |
| 6,117,902 A | * | 9/2000 | Quash et al. .................. 514/513 |
| 6,331,559 B1 | | 12/2001 | Bingham et al. |
| 6,605,637 B1 | | 8/2003 | Harnett et al. |
| 6,951,887 B2 | | 10/2005 | Bingham et al. |
| 2008/0262077 A1 | | 10/2008 | Shorr et al. |

FOREIGN PATENT DOCUMENTS

WO 00/24734 A1 5/2000

OTHER PUBLICATIONS

Bullock et al., Syntheses in the Thioctic Acid Series, 76 J. Am. Chem. Soc. 1828-32 (1954).*
Soper et al., Syntheses of DL-alpha-Lipoic Acid, 76 J. Am. Chem. Soc. 4109-12 (1954).*
Richard B. Silverman, The Organic Chemistry of Drug Design and Drug Action, Chapter 2: Drug Discovery, Design, and Development, Academic Press, p. 5-51 (1992).*
W. Hyk, et al., "The extreme migrational enhancement of faradaic current at microelectrodes: experimental studies on sodium (6,8-diferrocenylmethylthio)octanoate electrooxidation", Journal of Electroanalytical Chemistry 575, pp. 321-328 (2005).
S. Satoh, et al., "Simultaneous determination of alpha-lipoic acid and its reduced form by high-performance liquid chromatography with fluorescence detection", Journal of Chromatography B, 854, pp. 109-115 (2007).
D. Feller, et al., "Selective PPARgamma versus PPARalpha agonist activity of a novel set of alpha-lipoic acid analogs of thiazolidinediones", FASEB Journal, vol. 17, No. 4-5 (Mar. 2003), XP009133351; FASEB Meeting Experimental Biology: Translating the Genome, San Diago, CA (Apr. 2003).
Heather A.E. Benson, "Transdermal Drug Delivery: Penetration Enhancement Techniques", Current Drug Delivery, vol. 2, No. 1, pp. 23-33 (2005).
Surya Kanta De, "Yttrium Triflate As An Efficient and Useful Catalyst for Chemoselective Protection of Carbonyl Compounds", Tetrahedron Letters, vol. 45, pp. 2339-2341 (2004).
Handbook of Pharmaceutical Salts: Properties, Selection and Use, IUPAC, Wiley-VCH, P.H. Stahl ed., p. 342.

* cited by examiner

*Primary Examiner* — Janet L Andres
*Assistant Examiner* — Timothy R Rozof
(74) *Attorney, Agent, or Firm* — Goodwin Procter LLP

(57) ABSTRACT

Lipoic acid derivatives and pharmaceutical formulations containing lipoic acid derivatives are useful in the treatment and prevention of disease characterized by disease cells that are sensitive to lipoic acid derivatives.

11 Claims, No Drawings

LIPOIC ACID DERIVATIVES

This application claims the benefit of U.S. Provisional Patent Application No. 60/912,598, filed Apr. 18, 2007.

BACKGROUND OF THE INVENTION

1. Field of the Invention

The present invention is directed to lipoic acid derivatives or salts thereof which selectively kill tumor cells by altering cancer cell metabolism and signal transduction pathways linked to the Warburg Effect, as well as to methods of treating a subject with such lipoic acid derivatives.

2. Related Background Art

All mammalian cells require energy to live and grow. Cells obtain this energy by metabolizing food molecules by oxidative metabolism. The vast majority of normal cells utilize a single metabolic pathway to metabolize their food. The first step in this metabolic pathway is the partial degradation of glucose molecules to pyruvate in a process known as glycolysis which yields two ATP units. Glycolysis can occur even under hypoxic conditions. Pyruvate is further degraded in the mitochondrion by a process known as the tricarboxylic acid (TCA) cycle to produce thirty-six ATP units per glucose molecule, water and carbon dioxide. The TCA cycle requires oxygen. During periods of reduced oxygen levels, normal cells adapt by a variety of mechanisms and return to normal metabolism as oxygen levels are restored. A critical link between glycolysis and the TCA cycle is an enzyme known as pyruvate dehydrogenase ("PDH"). PDH is part of a larger multi-subunit complex (hereinafter "PDC"). PDH, in conjunction with other enzymes of the PDC complex, produces acetyl CoA which effectively funnels glycolysis-produced pyruvate to the TCA cycle.

Most cancers display profound perturbation of energy metabolism. One of the fundamental changes is the adoption of the Warburg Effect, where glycolysis becomes the main source of ATP. An ATP deficit follows reduced TCA ATP generation. In other words, cancer cells behave as if they are hypoxic even when they are not. This change in energy metabolism represents one of the most robust and well-documented correlates of malignant transformation and has been linked to other changes resulting in tumor growth and metastasis. Because of the reduced levels of ATP available as a result of glycolysis largely being de-linked from the TCA cycle, cancer cells increase their uptake of glucose and its conversion to pyruvate in an attempt to make up the energy deficit. Excess pyruvate and other metabolic by-products of the Warburg biochemistry must be managed. A number of these metabolites are known to be cytotoxic, e.g., acetaldehyde. PDC in cancer along with other related enzymes plays a major role in managing and/or detoxifying the excess pyruvate and metabolites. For example, the joining of two acetyl molecules to form the neutral compound acetoin. This generation of acetoin is catalyzed by a tumor-specific form of PDC.

It has been suggested that lipoic acid acts as a cofactor with PDC and related lipoamide using enzymes in detoxifying these otherwise toxic metabolites. Whether lipoic acid is made by healthy and cancer cells or whether it is an essential nutrient is debated in the literature, and both may be the case. The genes required to produce lipoic acid have been identified in mammalian cells. Whether mitochondrial pumps or uptake mechanisms are present in healthy or cancer cells or whether they differ in diverse tissues is not known. Although the TCA cycle still functions in cancer cells, the tumor cell TCA cycle is a variant cycle which depends on glutamine as the primary energy source. Inhibition or inactivation of tumor-specific PDC and related enzymes that detoxify metabolites may promote apoptosis or necrosis and cell death.

Despite extensive work characterizing the highly conserved changes among diverse tumor types and their metabolism, the changes remain to be successfully exploited as a target for cancer chemotherapy. As cancer remains the number two killer of Americans, there is an urgent need for new approaches to disease management. It has been suggested that lipoic acid due to its redox potential properties may be useful in the treatment of diverse diseases involving mitochondrial function such as diabetes, Alzheimers disease and cancer. These reports teach that the availability of the redox shift from SH to S—S be maintained to have the desired effect.

U.S. Pat. Nos. 6,331,559 and 6,951,887 disclose a novel class of therapeutic agents which selectively targets and kills tumor cells and certain other types of diseased cells. These patents further disclose pharmaceutical compositions comprising an effective amount of a lipoic acid derivative according to its invention along with a pharmaceutically acceptable carrier. The present inventors have now discovered additional lipoic acid derivatives beyond the scope of the aforementioned patents.

SUMMARY OF THE INVENTION

In a first aspect, the present invention is directed to a lipoic acid derivative having formula (I):

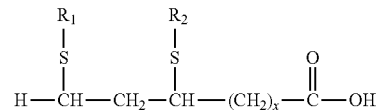

wherein $R_1$ and $R_2$ are independently selected from the group consisting of acyl defined as $R_3C(O)$, heteroaryl, imidoyl defined as $R_4C(=NH)—$, organometallic aryl, and alkyl-organometallic aryl; wherein $R_1$ and $R_2$ as defined above can be unsubstituted or substituted; wherein $R_3$ is selected from the group consisting of hydrogen, alkenyl, alkynyl, alkylaryl, heteroaryl, alkylheteroaryl and organometallic aryl, any of which can be substituted or unsubstituted; wherein $R_4$ is selected from the group consisting of hydrogen, alkenyl, alkynyl, aryl, alkylaryl, heteroaryl, and alkylheteroaryl, any of which can be substituted or unsubstituted; and wherein x is 0-16; or a salt thereof.

The present invention is further directed to a lipoic acid derivative having formula (I), wherein $R_1$ and $R_2$ are independently selected from the group consisting of acyl defined as $R_3C(O)$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_4C(=NH)—$, and hemiacetal defined as $R_5CH(OH)$—S—; wherein $R_1$ and $R_2$ as defined above can be unsubstituted or substituted; wherein $R_3$ and $R_4$ are independently selected from the group consisting of hydrogen, alkyl, alkenyl, alkynyl, cycloalkyl, aryl, alkylaryl, heteroaryl, and heterocyclyl, any of which can be substituted or unsubstituted; wherein $R_5$ is selected from the group consisting of $CCl_3$, $CF_3$ and COOH; and wherein x is 0-16, n is 0-10 and m is 2-10; provided that at least one of $R_1$ and $R_2$ is independently selected from the group consisting of acyl defined as $R_3C(O)$, heteroaryl, imidoyl defined as $R_4C(=NH)—$, organometallic aryl, and alkyl-organometallic aryl, with $R_3$ being selected from the group consisting of hydrogen, alkenyl, alkynyl, alkylaryl, heteroaryl, alkylheteroaryl, organometallic aryl, and alkyl-organometallic aryl, any of which can be substituted or unsubstituted, and $R_4$ being selected from the group consisting of hydrogen, alkenyl, alkynyl, aryl, alkylaryl, heteroaryl, and alkylheteroaryl, any of which can be substituted or unsubstituted; or a salt thereof.

Another embodiment of the invention is directed to a lipoic acid derivative having formula (I), wherein $R_1$ and $R_2$ are independently selected from the group consisting of acyl defined as $R_3C(O)$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_4C(=NH)$—, hemiacetal defined as $R_5CH(OH)$—S—, and hydrogen provided that at least one of $R_1$ and $R_2$ is hydrogen; wherein $R_1$ and $R_2$ as defined above can be unsubstituted or substituted; wherein $R_3$ is independently selected from the group consisting of hydrogen, alkenyl, alkynyl, cycloalkyl, aryl, alkylaryl, heteroaryl, alkylheteroaryl and heterocyclyl, any of which can be substituted or unsubstituted; wherein $R_4$ is independently selected from the group consisting of hydrogen, alkyl, alkenyl, alkynyl, cycloalkyl, aryl, alkylaryl, heteroaryl, and heterocyclyl, any of which can be substituted or unsubstituted; wherein $R_5$ is selected from the group consisting of $CCl_3$, $CF_3$ and COOH; and wherein x is 0-16, n is 0-10 and m is 2-10; or a salt thereof.

The invention is further directed to a lipoic acid derivative having formula (I), wherein $R_1$ and $R_2$ are independently selected from the group consisting of alkyl sulfide defined as $CH_3(CH_2)_n$—S— and hemiacetal defined as $R_5CH(OH)$—S—; wherein $R_1$ and $R_2$ as defined above can be unsubstituted or substituted and wherein at least one of $R_1$ and $R_2$ is substituted; wherein $R_5$ is selected from the group consisting of $CCl_3$, $CF_3$ and COOH; and wherein x is 0-16, n is 0-10 and m is 2-10; or a salt thereof.

A further embodiment of the invention is directed to a lipoic acid derivative having formula (I), wherein $R_1$ and $R_2$ are independently selected from the group consisting of acyl defined as $R_3C(O)$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_4C(=NH)$—, and hemiacetal defined as $R_5CH(OH)$—S—; wherein $R_1$ and $R_2$ as defined above can be unsubstituted or substituted; wherein $R_3$ and $R_4$ are independently selected from the group consisting of hydrogen, alkyl, alkenyl, alkynyl, cycloalkyl, aryl, alkylaryl, heteroaryl, and heterocyclyl, any of which can be substituted or unsubstituted; wherein $R_5$ is selected from the group consisting of $CCl_3$, $CF_3$ and COOH; and wherein x is 0-16, n is 0-10 and m is 2-10; provided that at least one of $R_1$ and $R_2$ is independently selected from the group consisting of an alkyl sulfide defined as $CH_3(CH_2)_n$—S— and hemiacetal defined as $R_5CH(OH)$—S—, said at least one of $R_1$ and $R_2$ being substituted; or a salt thereof.

The present invention is still further directed to a lipoic acid derivative having formula (II):

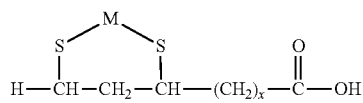

wherein M is —[C($R_1$)($R_2$)]$_z$—; wherein $R_1$ and $R_2$ are independently selected from the group consisting of acyl defined as $R_3C(O)$—, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_3C(=NH)$—, hemiacetal defined as $R_4CH(OH)$—S— and hydrogen; wherein $R_1$ and $R_2$ as defined above can be unsubstituted or substituted; wherein $R_3$ and $R_4$ are independently selected from the group consisting of hydrogen, alkyl, alkenyl, alkynyl, cycloalkyl, aryl, alkylaryl, heteroaryl, and heterocyclyl, any of which can be substituted or unsubstituted; wherein $R_5$ is selected from the group consisting of $CCl_3$, $CF_3$ or COOH; and wherein x is 0-16, z is 0-5, n is 0-10 and m is 2-10; or a salt thereof.

Further embodiments of the present invention include those having formula (I) in which one or both of the $R_1$ and $R_2$ groups include an alkylaryl substituent, an alkyl substituent with a heteroatom in the carbon chain, a substituted acyl group or a substituted alkyl group.

A still further embodiment of the present invention is directed to a pharmaceutical formulation comprising (a) a therapeutically effective amount of at least one lipoic acid derivative of any of the embodiments of the invention and (b) at least one pharmaceutically acceptable additive. In preferred embodiments, the at least one pharmaceutically acceptable additive is selected from solvents, diluents, surfactants, solubilizers, preservatives, buffers, and combinations thereof and/or the at least one lipoic acid derivative is present in an amount to provide from about 0.001 mg/m² to about 10 g/m².

Still further embodiments of the invention are directed to methods of treating or preventing a disease characterized by disease cells that are sensitive to lipoic acid derivatives comprising administering to a patient in need thereof a therapeutically effective amount of at least one lipoic acid derivative according to any of the embodiments of the invention. In preferred embodiments, the at least one lipoic acid derivative is in a pharmaceutical formulation further comprising at least one pharmaceutically acceptable additive.

DETAILED DESCRIPTION

The present invention is directed to lipoic acid derivatives which are effective to target and kill tumor cells. Accordingly, in a first embodiment, the present invention is directed to a lipoic acid derivative having formula (I):

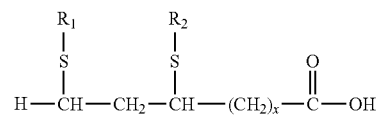

wherein $R_1$ and $R_2$ are independently selected from the group consisting of acyl defined as $R_3C(O)$, heteroaryl, imidoyl defined as $R_4C(=NH)$—, organometallic aryl, and alkyl-organometallic aryl;

wherein $R_1$ and $R_2$ as defined above can be unsubstituted or substituted;

wherein $R_3$ is selected from the group consisting of hydrogen, alkenyl, alkynyl, alkylaryl, heteroaryl, alkylheteroaryl and organometallic aryl, any of which can be substituted or unsubstituted;

wherein $R_4$ is selected from the group consisting of hydrogen, alkenyl, alkynyl, aryl, alkylaryl, heteroaryl, and alkylheteroaryl, any of which can be substituted or unsubstituted; and wherein x is 0-16;

or a salt thereof.

In a second embodiment, the present invention is directed to a lipoic acid derivative having formula (I):

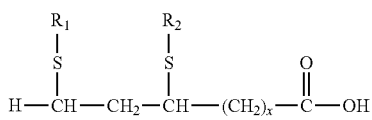

wherein $R_1$ and $R_2$ are independently selected from the group consisting of acyl defined as $R_3C(O)$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_4C(=NH)$—, and hemiacetal defined as $R_5CH(OH)$—S—;

wherein $R_1$ and $R_2$ as defined above can be unsubstituted or substituted;

wherein $R_3$ and $R_4$ are independently selected from the group consisting of hydrogen, alkyl, alkenyl, alkynyl, cycloalkyl, aryl, alkylaryl, heteroaryl, and heterocyclyl, any of which can be substituted or unsubstituted;

wherein $R_5$ is selected from the group consisting of $CCl_3$, $CF_3$ and COOH; and wherein x is 0-16, n is 0-10 and m is 2-10;

provided that at least one of $R_1$ and $R_2$ is independently selected from the group consisting of acyl defined as $R_3C(O)$, heteroaryl, imidoyl defined as $R_4C(=NH)$—, organometallic aryl, and alkyl-organometallic aryl, with $R_3$ being selected from the group consisting of hydrogen, alkenyl, alkynyl, alkylaryl, heteroaryl, alkylheteroaryl, organometallic aryl, and alkyl-organometallic aryl, any of which can be substituted or unsubstituted, and $R_4$ being selected from the group consisting of hydrogen, alkenyl, alkynyl, aryl, alkylaryl, heteroaryl, and alkylheteroaryl, any of which can be substituted or unsubstituted;

or a salt thereof.

Particularly preferred lipoic acid derivatives of the first and second embodiments include:

(A)

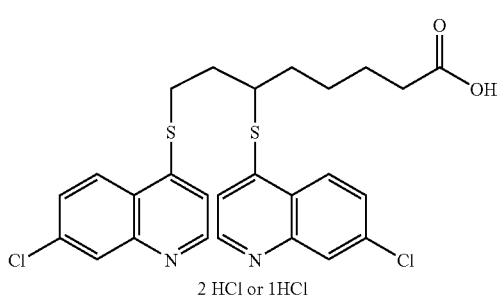

2 HCl or 1HCl (B)

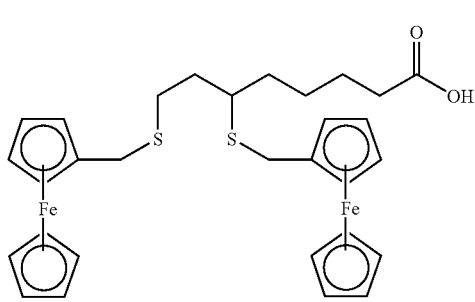

(C)

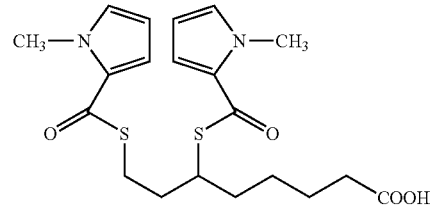

(D)

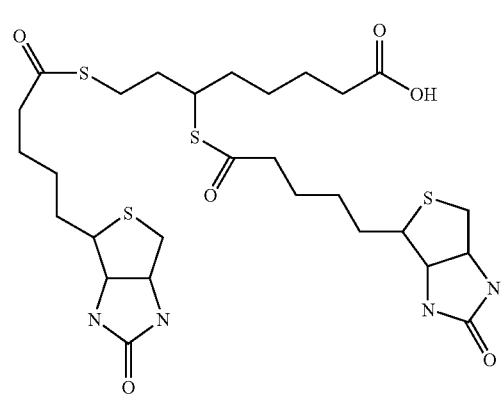

(E)

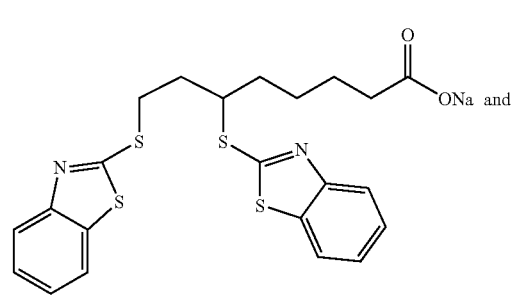

and (F)

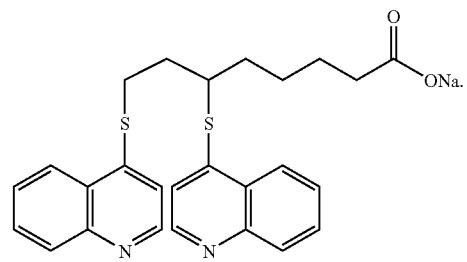

In a third embodiment, the present invention is directed to a lipoic acid derivative having formula (I):

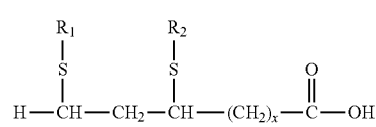

wherein $R_1$ and $R_2$ are independently selected from the group consisting of acyl defined as $R_3C(O)$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3$ $(CH_2)_n$—S—, imidoyl defined as $R_4C(=NH)$—, hemiacetal defined as $R_5CH(OH)$—S—, and hydrogen provided that at least one of $R_1$ and $R_2$ is hydrogen;

wherein $R_1$ and $R_2$ as defined above can be unsubstituted or substituted;

wherein $R_3$ is independently selected from the group consisting of hydrogen, alkenyl, alkynyl, cycloalkyl, aryl, alkylaryl, heteroaryl, alkylheteroaryl and heterocyclyl, any of which can be substituted or unsubstituted;

wherein $R_4$ is independently selected from the group consisting of hydrogen, alkyl, alkenyl, alkynyl, cycloalkyl, aryl, alkylaryl, heteroaryl, and heterocyclyl, any of which can be substituted or unsubstituted;

wherein $R_5$ is selected from the group consisting of $CCl_3$, $CF_3$ and COOH; and wherein x is 0-16, n is 0-10 and m is 2-10;

or a salt thereof.

Particularly preferred lipoic acid derivatives of the third embodiment include:

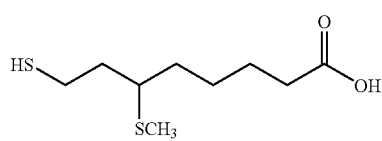
(G)

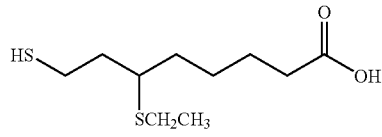
(H)

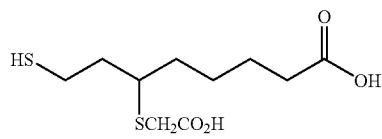
(I)

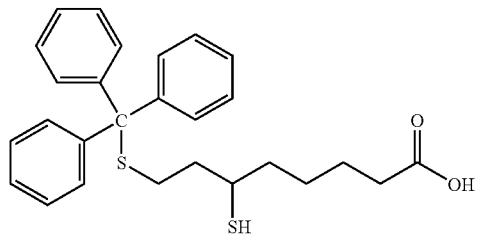
(J)

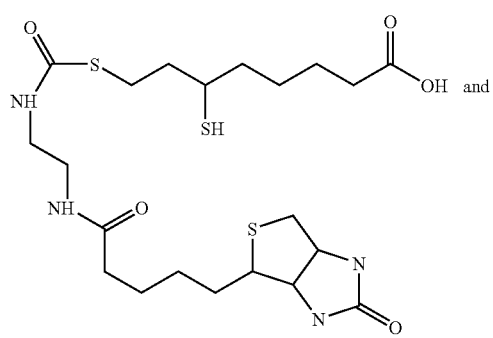
(K)

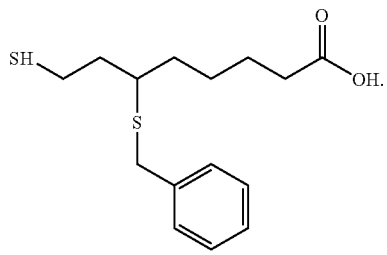
(L)

In a fourth embodiment, the present invention is directed to a lipoic acid derivative having formula (I):

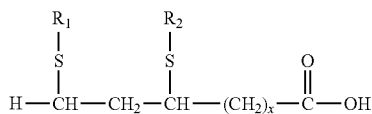

wherein $R_1$ and $R_2$ are independently selected from the group consisting of alkyl sulfide defined as $CH_3(CH_2)_n$—S— and hemiacetal defined as $R_5CH(OH)$—S—;

wherein $R_1$ and $R_2$ as defined above can be unsubstituted or substituted and wherein at least one of $R_1$ and $R_2$ is substituted;

wherein $R_5$ is selected from the group consisting of $CCl_3$, $CF_3$ and COOH; and wherein x is 0-16, n is 0-10 and m is 2-10;

or a salt thereof.

In a fifth embodiment, the present invention is directed to a lipoic acid derivative having formula (I):

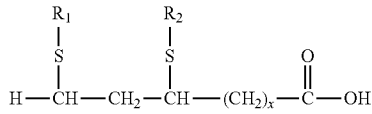

wherein $R_1$ and $R_2$ are independently selected from the group consisting of acyl defined as $R_3C(O)$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_4C(=NH)$—, and hemiacetal defined as $R_5CH(OH)$—S—;

wherein $R_1$ and $R_2$ as defined above can be unsubstituted or substituted;

wherein $R_3$ and $R_4$ are independently selected from the group consisting of hydrogen, alkyl, alkenyl, alkynyl, cycloalkyl, aryl, alkylaryl, heteroaryl, and heterocyclyl, any of which can be substituted or unsubstituted;

wherein $R_5$ is selected from the group consisting of $CCl_3$, $CF_3$ and COOH; and wherein x is 0-16, n is 0-10 and m is 2-10;

provided that at least one of $R_1$ and $R_2$ is independently selected from the group consisting of an alkyl sulfide defined as $CH_3(CH_2)_n$—S— and hemiacetal defined as $R_5CH(OH)$—S—, said at least one of $R_1$ and $R_2$ being substituted;

or a salt thereof.

Particularly preferred lipoic acid derivatives of the fourth and fifth embodiments include:

(JJ)

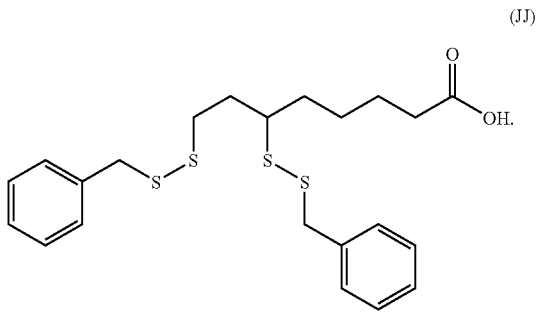 [SMILES: O=C(O)CCCCC(CCSSCc1ccccc1)SSCc1ccccc1]

In a sixth embodiment of this invention, the lipoic acid derivative has the formula (II):

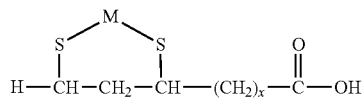

M is —[C(R$_1$)(R$_2$)]$_z$—, where R$_1$ and R$_2$ are independently selected from the group consisting of acyl defined as R$_3$C(O)—, alkyl defined as C$_n$H$_{2n+1}$, alkenyl defined as C$_m$H$_{2m-1}$, alkynyl defined as C$_m$H$_{2m-3}$, aryl, heteroaryl, alkyl sulfide defined as CH$_3$(CH$_2$)$_n$—S—, imidoyl defined as R$_3$C(=NH)—, hemiacetal defined as R$_4$CH(OH)—S— and hydrogen, wherein R$_1$ and R$_2$ as defined above can be unsubstituted or substituted. R$_3$ and R$_4$ are independently selected from the group consisting of hydrogen, alkyl, alkenyl, alkynyl, cycloalkyl, aryl, alkylaryl, heteroaryl, and heterocyclyl, any of which can be substituted or unsubstituted; R$_5$ is selected from the group consisting of CCl$_3$, CF$_3$ or COOH. In addition, x is 0-16, z is preferably 0-5, more preferably 0-3, n is 0-10 and m is 2-10. Suitable —[C(R$_1$)(R$_2$)]$_z$— groups include, without limitation, —CH$_2$, —CH(CH$_3$), —C(CH$_3$)$_2$, —CH(C$_6$H$_5$) and —CH(pyridine).

Particularly preferred lipoic acid derivatives of the sixth embodiment include:

(M)

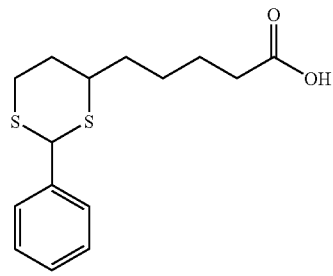

(N)

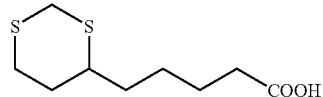

(O)

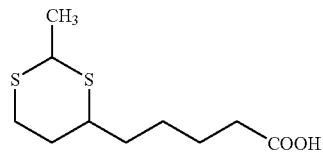

(P)

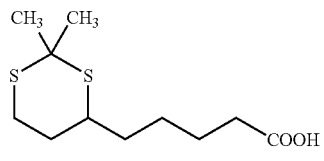

(Q)

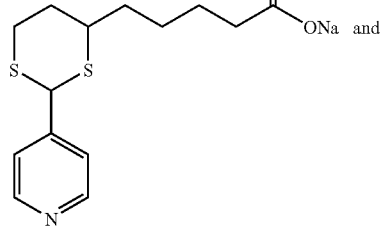

(R)

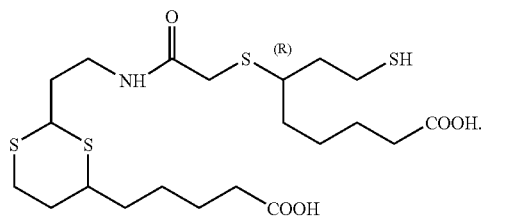

As used herein, acyl refers to an R$_3$C(O)— group, where R$_3$ can be, without limitation, hydrogen, alkyl, alkenyl, alkynyl, cycloalkyl, aryl, alkylaryl, heteroaryl, or heterocyclyl, any of which can be substituted or unsubstituted. In certain embodiments of the invention, R$_3$ is hydrogen, alkenyl, alkynyl, alkylaryl, heteroaryl, alkylheteroaryl or organometallic aryl, any of which can be substituted or unsubstituted; in other embodiments, R$_3$ is hydrogen, alkenyl, alkynyl, cycloalkyl, aryl, alkylaryl, heteroaryl, alkylheteroaryl, or heterocyclyl, any of which can be substituted or unsubstituted. In other words, one of the listed R$_3$ groups is linked to the carbon backbone of formula (I) through a thio-ester linkage. Examples of acyl groups include, without limitation, acetyl, benzoyl and benzoyl derivatives, 4-fluorobenzoyl and 1-methylpyrrole-2-carboxyl.

As used herein, alkyl refers to a C$_n$H$_{2n+1}$ group, wherein n is 1-10, more preferably 1-6 and most preferably 1-4, i.e., an alkyl group linked to the carbon backbone of formula (I) through a thio-ether linkage. Alkyl groups can be either aliphatic (straight or branched chain) or alicyclic; alicyclic groups may have additions or substitutions on any of the carbons to form heterocyclics. At least one heteroatom such as N, O or S may be present in a given alkyl group, i.e., in the carbon chain. Alkyl groups may be substituted or unsubstituted on any of their carbons. A preferred alkyl group is an alkyl group substituted with an aryl or heteroaryl group, i.e., wherein R$_1$ or R$_2$ is an alkylaryl or alkylheteroaryl group; the aryl or heteroaryl group may be substituted or unsubstituted. Examples of alkyl groups include, without limitation, methyl, ethyl, butyl, decanyl, cyclopropyl, 4-pyridine methyl, 2-anthraquinone methyl, N-phenylacetamide, phenylethyl, 2-ethanoic acid, 2-acetamido, 4-(2-acetamido-pyridinyl)methyl, N-[(2-fluorophenyl)methyl]acetamide, N-[(6-methoxy-3-pyridyl)methyl]acetamide, 5-(acetylamino)pyridine-2-carboxamide, 5-(6,8-diaza-7-oxo-3-thiabicyclo[3.3.0]oct-2-yl)-N-(2-carbonylaminoethyl)pentanamide and 5-(6,8-diaza-7-oxo-3-thiabicyclo[3.3.0]oct-2-yl)pentacarboxyl.

As used herein, alkenyl refers to a $C_mH_{2m-1}$ group, wherein m is 2-10, i.e., an alkenyl group linked to the carbon backbone of formula (I) through a thio-ether linkage. Alkenyl groups can be either aliphatic (straight or branched chain) or alicyclic; alicyclic groups may have additions or substitutions on any of the carbons to form heterocyclics. At least one heteroatom such as N, O or S may be present in a given alkenyl group, i.e., in the carbon chain. Alkenyl groups may be substituted or unsubstituted on any of their carbons. Examples of alkenyl groups include, without limitation, propenyl, 2,3 dimethyl-2-butenyl, heptenyl and cyclopentenyl.

As used herein, alkynyl refers to a $C_mH_{2m-3}$, where m is 2-10, i.e., an alkynyl group linked to the carbon backbone of formula (I) through a thio-ether linkage. Alkynyl groups can be either aliphatic (straight or branched chain) or alicyclic; alicyclic groups may have additions or substitutions on any of the carbons to form heterocyclics. At least one heteroatom such as N, O or S may be present in a given alkynyl group, i.e., in the carbon chain. Alkynyl groups may be substituted or unsubstituted on any of their carbons. Examples of alkynyl groups include, without limitation, acetylenyl, propynyl and octynyl.

As used herein, aryl refers to an aromatic or aryl group linked to the carbon backbone of formula (I) through a thio-ether linkage. Aryl is preferably an unsaturated ring system having 6-10 carbon atoms. Aryl also includes organometallic aryl groups such as ferrocene. Aryl groups may be substituted or unsubstituted on any of their carbons. Examples of aryl groups include, without limitation, benzyl ($-CH_2C_6H_5$), benzyl derivatives such as methylbenzyl and aminobenzyl, (1,2,3,4,5-pentafluorophenyl)methyl, triphenylmethyl, 4-methyl benzoic acid, ferrocene methyl, 2-naphthylmethyl, 4,4-biphenylmethyl, and stilbene (or 1-((1E)-2-phenylvinyl)-4-methyl benzene).

As used herein, heteroaryl refers to an aromatic heterocyclic ring system (monocyclic or bicyclic) where the heteroaryl moieties are five- or six-membered rings containing 1 to 4 heteroatoms selected from the group consisting of S, N, and O; the heteroaryl group is linked to the carbon backbone of formula (I) through a thio-ether linkage. Heteroaryl groups may be substituted or unsubstituted on any of their atoms especially on the carbon atoms. Examples of heteroaryl groups include, without limitation, benzothiazole, quinoline, 7-chloroquinoline, furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzofuran, benzisoxazole, benzimidazole, N-methylbenzimidazole, azabenzimidazole, indazole, quinazoline and pyrrolidinyl.

As used herein, alkyl sulfide refers to a $CH_3(CH_2)_n$—S— group, where n is 0-9. In other words, an alkyl group is linked to the carbon backbone of formula (I) through a disulfide linkage. The alkyl group (i.e., $CH_3(CH_2)_n$) can be substituted or unsubstituted on any of its carbons and shares the same features as set forth above with regard to the $C_nH_{2n+1}$ alkyl group.

As used herein, imidoyl refers to a $R_4C(=NH)$— group, where $R_4$ can be, without limitation, hydrogen, alkyl, alkenyl, alkynyl, cycloalkyl, aryl, alkylaryl, heteroaryl, or heterocyclyl, any of which can be substituted or unsubstituted. In certain embodiments of the invention, $R_4$ is hydrogen, alkenyl, alkynyl, aryl, alkylaryl, heteroaryl and alkylheteroaryl, any of which can be substituted or unsubstituted. In other words, one of the listed $R_4$ groups is linked to the carbon backbone of formula (I) through a thio-imide linkage.

As used herein, hemiacetal refers to an $R_5CH(OH)$—S— group, where $R_5$ is a compound with a strongly electron withdrawing substituent such as, without limitation, $CF_3$, $CCl_3$ or COOH.

Any of the above-described groups can be unsubstituted or substituted. Exemplary substituents include, without limitation, alkyl, alkenyl, alkynyl, aryl, heteroaryl, acyl, alkoxycarbonyl, alkoxy, alkoxyalkyl, alkoxyalkoxy, cyano, halogen, hydroxy, nitro, oxo, trifluoromethyl, trifluoromethoxy, trifluoropropyl, amino, amido, alkylamino, dialkylamino, dialkylaminoalkyl, hydroxyalkyl, alkoxyalkyl, alkylthio, $-SO_3H$, $-SO_2NH_2$, $-SO_2NHalkyl$, $-SO_2N(alkyl)_2$, $-CO_2H$, $CO_2NH_2$, $CO_2NHalkyl$, and $-CO_2N(alkyl)_2$. In addition, any number of substitutions may be made on any of the above-described groups; in other words, it is possible to have a mono-, di-, tri-, etc. substituted $R_1$ or $R_2$ group, and the substituents themselves may also be substituted. Further, any of the $R_1$ or $R_2$ groups may be appropriately generally substituted with any of a carbohydrate, a lipid, a nucleic acid, an amino acid or a polymer of any of those, or a single or branched chain synthetic polymer (having a molecular weight ranging from about 350 to about 40,000).

For any definition of $R_1$ and $R_2$ noted above, the thio-ester or thio-ether linkage by which the $R_1$ and $R_2$ are linked to the backbone can be oxidized to produce sulfoxides or sulfones; in other words, the —S— in the linkage could be —S(O)— or —S(O)$_2$. In addition, for any definition of $R_1$ and $R_2$ noted above, the thio-ester or thio-ether linkage by which the $R_1$ and $R_2$ are linked to the backbone may further comprise disulfides that can be oxidized to thiosulfinic or thiosulfonic acids; in other words, instead of —S— in a linkage, the linkage could be —S(O)—S— or —S(O)$_2$—S—.

Regardless of whether the lipoic acid derivative is of formula (I) or formula (II), lipoic acid derivatives of the present invention may include those in which one or both of the thiols have been replaced with a selenium molecule, a sulfur analog, or in which one or both of the thiols have been oxidized to sulfate or related groups.

Additional preferred lipoic acid derivatives of the present invention include certain compounds of formula (I) in which an alkylaryl substituent for one or both of $R_1$ and $R_2$ is present. Such lipoic acid derivatives include:

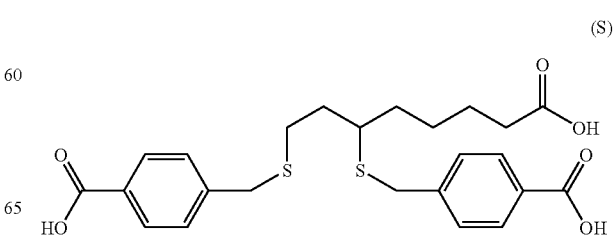

(T)
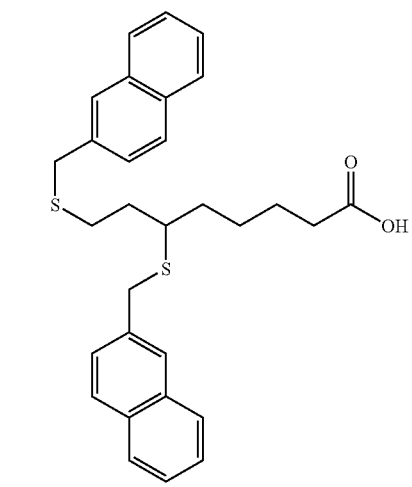
(U)
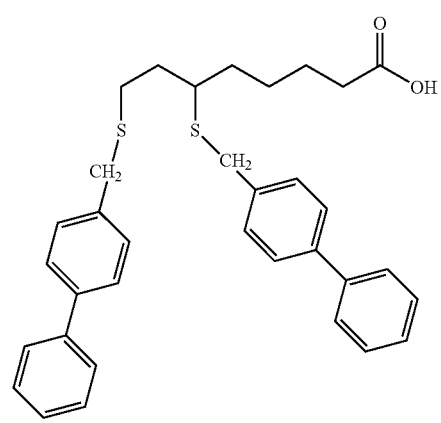
(V)
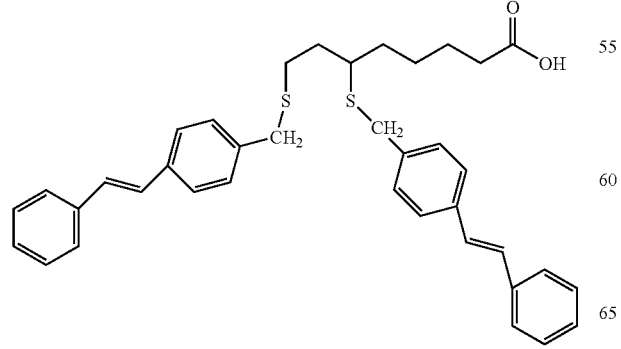
(W)
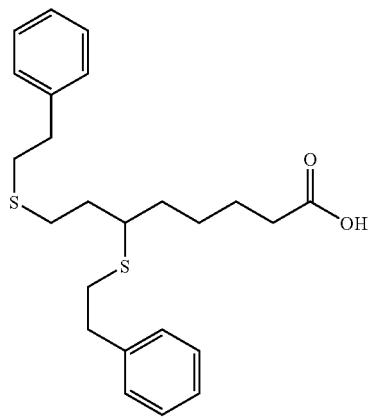
(X)
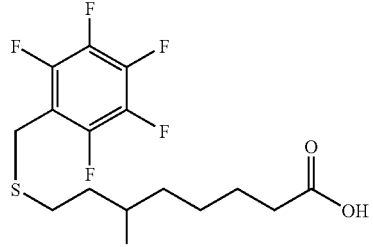
(Y)
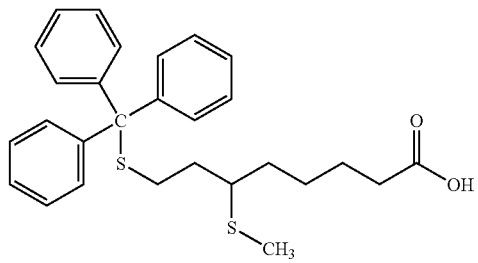
(Z)
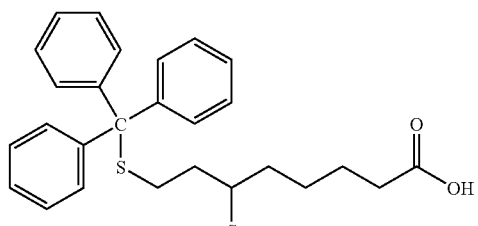
(AA)
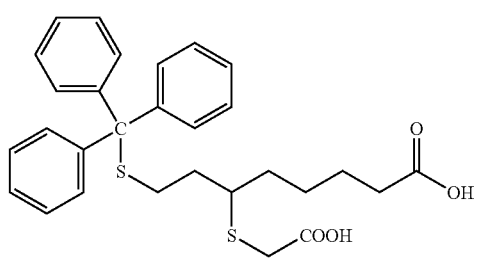

-continued (BB)
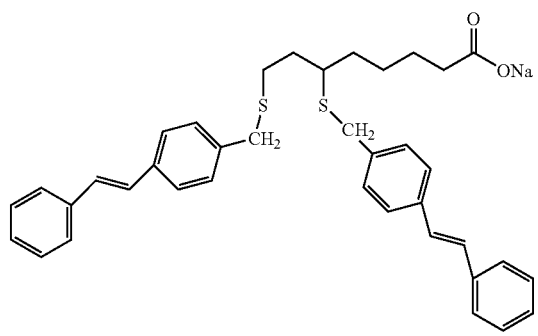

and (KK)
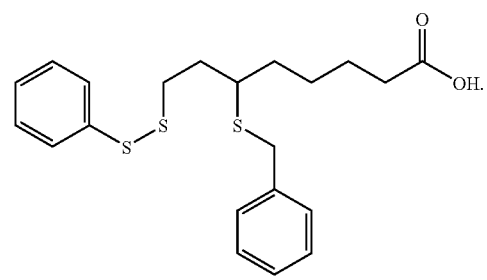

Still other preferred embodiments of the present invention include the following lipoic acid derivatives in which an alkyl group with a heteroatom substitution is present for one or both of $R_1$ and $R_2$:

(CC)
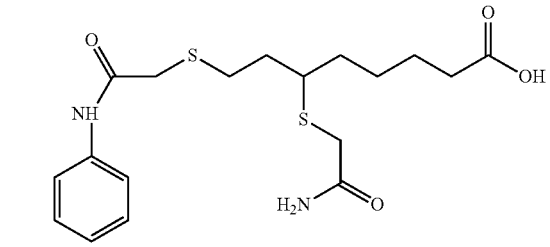

(DD)
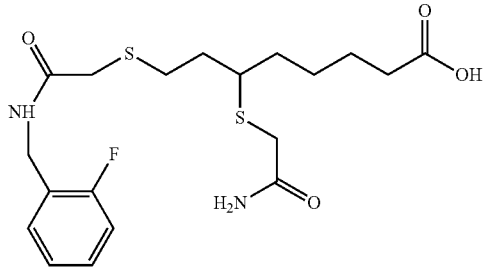

-continued (EE)
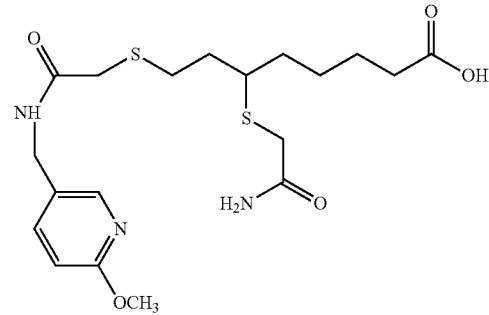

(FF)
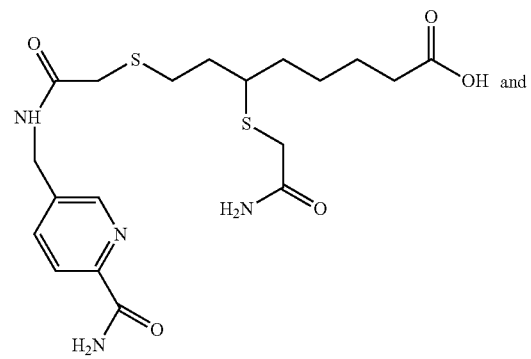 and (LL)
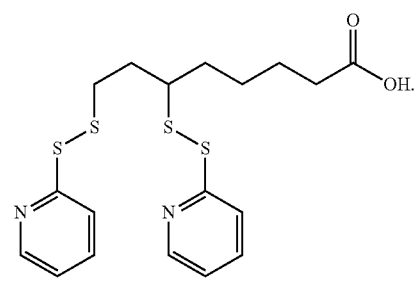

Another preferred embodiment of the present invention is directed to the following lipoic acid derivative which includes a substituted acyl group:

(GG)
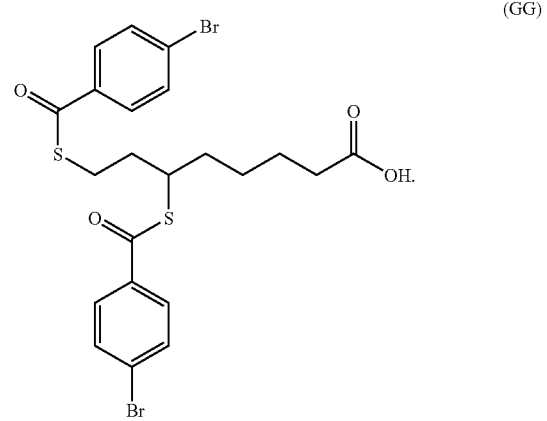 [SMILES: O=C(O)CCCCC(CCSC(=O)c1ccc(Br)cc1)SC(=O)c1ccc(Br)cc1]

Still additional preferred embodiments of the present invention include the following asymmetrically substituted lipoic acid derivatives:

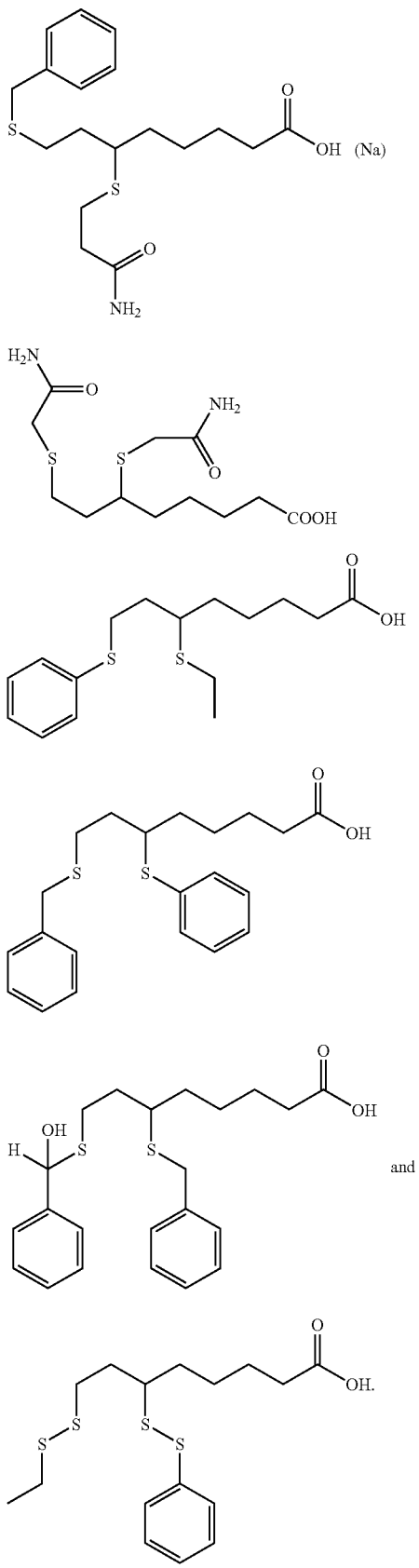

A further embodiment of the present invention is directed to a pharmaceutical formulation comprising (a) a therapeutically effective amount of at least one lipoic acid derivative of any one of the previously set forth (above) embodiments and (b) at least one pharmaceutically acceptable additive.

Typically the at least one lipoic acid derivative is present in a pharmaceutical formulation of the present invention in a therapeutically effective amount. The pharmaceutical formulation of the present invention may contain a unit dose or multiple doses of the lipoic acid derivative. A "therapeutically effective amount" is intended to mean the amount of a lipoic acid derivative that, when administered to a subject in need thereof, is sufficient to effect treatment for (or prevent) disease conditions characterized by disease cells that are sensitive to lipoic acid derivatives. The amount of a given lipoic acid derivative that will be therapeutically effective will vary depending upon factors such as the disease condition and the severity thereof, the identity of the subject in need thereof, etc., which amount may be routinely determined by artisans of ordinary skill in the art. Importantly, the quantity of lipoic acid derivative in a unit dose should be sufficient to inhibit or kill tumor cells while leaving normal cells substantially unharmed. The at least one lipoic acid derivative is preferably present in a pharmaceutical formulation of the present invention in an amount to provide from about 0.001 mg/m$^2$ to about 10 g/m$^2$, more preferably about 0.01 mg/m$^2$ to about 5 g/m$^2$, still more preferably from about 0.25 mg/m$^2$ to about 3 g/m$^2$, and most preferably from about 20 mg/m$^2$ to about 500 mg/m$^2$ of the at least one lipoic acid derivative per dose.

Pharmaceutically acceptable additives suitable for use in the present invention include, without limitation, solvents, diluents, surfactants, solubilizers, preservatives, buffers, and combinations thereof, as well as any other additives particularly suited for use in parenteral administration forms. It is well within the skill of one of ordinary skill in the art to determine suitable amounts of these pharmaceutically acceptable additives. Solvents particularly suitable for use herein include benzyl alcohol, dimethylamine, isopropyl alcohol and combinations thereof; one of ordinary skill in the art would readily recognize that it may be desirable to first dissolve the at least one lipoic acid derivative in a suitable solvent and then to dilute the solution with a diluent.

When a pharmaceutical formulation suitable for, e.g., intravenous administration is desired, a suitable diluent would be employed. Any conventional aqueous or polar aprotic solvent is suitable for use in the present invention. Suitable pharmaceutically acceptable diluents include, without limitation, saline, a sugar solution, alcohols such as ethyl alcohol, methanol and isopropyl alcohol, polar aprotic solvents such as dimethylformamide (DMF), dimethylsulfoxide (DMSO) and dimethylacetamide (DMA), and combinations thereof. A preferred pharmaceutically acceptable diluent is a dextrose solution, more preferably a dextrose solution containing from about 2.5% to about 10%, more preferably about 5%, dextrose by weight. The pharmaceutically acceptable diluent is typically employed in a non-homolysis generating amount; one of ordinary skill in the art can readily determine an amount of diluent suitable for use in a pharmaceutical formulation according to the present invention.

The pharmaceutical formulations of the present invention can be prepared according to conventional formulation techniques. For example, a stock solution of the at least one lipoic acid derivative can be prepared according to conventional techniques and then diluted as desired by a pharmaceutically acceptable diluent. Pharmaceutical formulations of the lipoic acid derivatives of the present invention may also be prepared in accordance with the details set forth in co-pending U.S.

Provisional Application No. 60/912,605, filed Apr. 18, 2007, the entire disclosure of which is incorporated by reference herein.

The pharmaceutical formulations of the present invention are liquid preparations such as sterile parenteral solutions. The pharmaceutical formulations of the present invention may be contained in any suitable vessel such as a vial or ampoule and are suitable for administration via one of several routes including, without limitation, intravenous, intramuscular, subcutaneous, intradermally, intraperitoneal, intrathoracic, intrapleural, intrauterine or intratumor.

Further embodiments of the invention are directed to pharmaceutical formulations which are suitable for types of administration other than those listed above, for example and without limitation, oral, nasal, topical, transdermal, and rectal. The pharmaceutical formulations of this invention may take any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols.

A further embodiment of the invention is directed to a method of treating a disease characterized by disease cells that are sensitive to lipoic acid derivatives comprising administering to a patient in need thereof a therapeutically effective amount of at least one lipoic acid derivative according to the present invention. Preferably, the at least one lipoic acid derivative is incorporated into a pharmaceutical formulation according to the present invention. A still further embodiment of the invention is directed to a method of preventing a disease characterized by disease cells that are sensitive to lipoic acid derivatives comprising administering to a patient in need thereof a therapeutically effective amount of at least one lipoic acid derivative according to the present invention. Preferably, the at least one lipoic acid derivative is incorporated into a pharmaceutical formulation according to the present invention.

According to the methods of treatment and prevention, lipoic acid derivatives and pharmaceutical formulations of lipoic acid derivatives of the present invention may be used to prevent or inhibit diseases involving altered or distinct cellular PDC activity, i.e., diseases characterized by disease cells that are sensitive to lipoic acid derivatives. Cells with appropriately altered or deranged energy metabolism, i.e., altered PDC activity, are particularly targeted and killed, while surrounding healthy tissues remain unharmed by the lipoic acid derivative. The skilled artisan can readily identify diseases having altered PDC activity. Alternatively, the skilled artisan can readily screen the disease of interest for sensitivity to lipoic acid derivatives.

In preferred embodiments of the methods of the present invention, the disease treated or prevented includes cancer, such as carcinoma, sarcoma, myeloma, lymphoma, leukemia and mixed types thereof. The pharmaceutical formulations of the present invention are effective against both primary and metastatic cancers and effective against cancers of the, without limitation, lung, liver, uterus, cervix, bladder, kidney, colon, breast, prostate, ovary, and pancreas. In other embodiments, the pharmaceutical formulations of the present invention can be used in the treatment of diseases associated with altered energy metabolism such as Alzheimer's disease, hyperproliferative diseases such as psoriasis and other diseases such as diabetic neuropathy.

For therapeutic applications, a lipoic acid derivative or a pharmaceutical formulation according to the invention is administered directly to a patient, typically in a unit dose form. In the methods of this invention, the lipoic acid derivative or pharmaceutical formulation comprising the lipoic acid derivative may be administered via one of several routes including, without limitation, intravenous, intramuscular, subcutaneous, intradermally, intraperitoneal, intrathoracic, intrapleural, intrauterine or intratumor. Those skilled in the art will recognize that the mode of administering the lipoic acid derivative depends on the type of cancer or symptom to be treated. For example, a preferred mode of administering the lipoic acid for treatment of leukemia would involve intravenous administration. Likewise, those skilled in the art will also recognize that particular pharmaceutically acceptable additives will vary from pharmaceutical formulations suitable for one administration mode to pharmaceutical formulations suitable for another administration mode.

By adapting the treatments described herein, the lipoic acid derivatives or the pharmaceutical formulations of the present invention may also be used in methods for treating diseases other than cancer, where the disease-causing cells exhibit altered metabolic patterns. For example, eukaryotic pathogens of humans and other animals are generally much more difficult to treat than bacterial pathogens because eukaryotic cells are so much more similar to animal cells than are bacterial cells. Such eukaryotic pathogens include protozoans such as those causing malaria as well as fungal and algal pathogens. Because of the remarkable lack of toxicity of the lipoic acid derivatives of the invention to normal human and animal cells and because many eukaryotic pathogens are likely to pass through life cycle stages in which their PDCs become sensitive to lipoic acid derivatives, the lipoic acid derivatives and pharmaceutical formulations of the present invention can be used to kill bacterial PDCs.

Specific embodiments of the invention will now be demonstrated by reference to the following examples. It should be understood that these examples are disclosed solely by way of illustrating the invention and should not be taken in any way to limit the scope of the present invention.

Synthesis of 6,8-Bismercaptooctanoic Acid
(Intermediate)

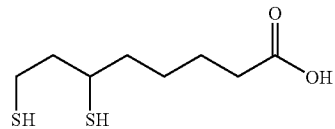 [SMILES: O=C(O)CCCCC(S)CCS]

α-Lipoic acid (5.15 g, 25.0 mmol) was suspended in water (125 mL), and sodium bicarbonate (2.1 g, 25.0 mmol) was added. The mixture was stirred to produce a clear solution. The resulting pale yellow solution was cooled in an ice bath, and solid sodium borohydride (1.90 g, 50.0 mmol) was added, with stirring, in small portions over 20 min. The solution was stirred in an ice bath for another 30 min and then at room temperature for 30 min. The cloudy solution was cooled in an ice bath, and the pH was adjusted to 1 by slow addition of 2M hydrochloric acid. A vigorous evolution of hydrogen occurred as the excess sodium borohydride decomposed, and an oily liquid was seen to separate. The mixture was extracted with chloroform (3×50 mL). The combined chloroform extracts were dried over magnesium sulfate, filtered and the solvent evaporated under reduced pressure at room temperature. The remaining oil was further dried under vacuum to remove traces of solvent. 6,8-Bismercaptooctanoic acid was isolated as a colorless oil: 5.2 g (100%). The product was stored at −20° C. under nitrogen. $^1$H-NMR (CDCl$_3$): δ 2.89 (m, 1H, S—C—H). 2.67 (m, 2H, S—CH$_2$), 2.34 (t, J=7.1 Hz, 2H, CH$_2$C(O)), 1.4-1.92 (m, 8H, (CH$_2$)$_2$), 1.33 (t, J=8.0 Hz, 1H, S—H), 1.30 (t, J=7.6 Hz, 1H, S—H).

EXAMPLE 1

General Procedure for Compounds (A), (E) and (F)

6,8-Bismercaptooctanoic acid (1eq.), obtained as described above, was dissolved in absolute ethanol. To this solution, the appropriate aryl chloride (2.2eq.) was added. The resulting solution was treated with a freshly prepared sodium ethoxide solution (sodium (4.4eq.) was added in small portions, under nitrogen, to absolute ethanol to form freshly prepared sodium ethoxide). The reaction mixture was refluxed under nitrogen for 4-6 h. The reaction mixture was then cooled in an ice bath and acidified carefully with 2N HCl, to a pH of 2-3. The acidic aqueous phase was extracted with chloroform (×3), and the combined chloroform extracts were washed with water (×1), sat. aq. NaCl (×1), and dried (MgSO$_4$). Evaporation of the chloroform gave the crude product. The products were purified by column chromatography on silica gel with chloroform:methanol (9:1) as the eluent.

For compounds obtained as sodium salts, the acidification step described above was omitted. The reaction mixture, upon evaporation of the solvents, was dissolved in chloroform, and ether was added to precipitate the sodium salt which was filtered and dried in vacuo.

EXAMPLE 2

General Procedures for S-Acylated Compounds (C), (D) and (GG)

Procedure 1: 6,8-Bismercaptooctanoic acid was acylated with three equivalents of the appropriate acyl chloride in the presence of triethylamine to produce 6,8-bisacylmercaptooctanoic acylanhydride. The anhydride was selectively hydrolyzed with dioxane/water to produce 6,8-bisacylmercaptooctanoic acid without any undesired hydrolysis of the benzoylthio ester groups. The product was purified by column chromatography on silica gel.

General example of procedure 1-synthesis of 6,8-bisbenzoylmercaptooctanoic acid: 6,8-Bismercaptooctanoic acid (2.03 g, 10 mmol) was dissolved in dry methylene chloride (50 mL) under nitrogen, and triethylamine (3.24 g, 32 mmol) was added. Benzoyl chloride (4.50 g, 32 mmol) in methylene chloride (20 mL) was added dropwise, with stirring, over 20 min. The salt that was formed between triethylamine and HCl precipitated during this addition. The solution itself remained colorless. Stirring was continued at room temperature for 9 h. The volume was increased to 100 mL with more methylene chloride (the entire solid dissolved), and the solution was transferred to a separatory funnel. It was extracted with 10% citric acid (2×50 mL, the pH of the aqueous phase was checked after the extraction to be sure it was acidic), and then washed with saturated aq. NaCl (50 mL). The organic phase was dried over magnesium sulfate, filtered, and the methylene chloride evaporated. A colorless oil was obtained. The above oil (5.48 g) was dissolved in dioxane (20 mL), and water (20 mL) was added. This caused the material to form an oil. The mixture was stirred at 40-45° C. for 53 h. The solvent was evaporated under vacuum (2 mm) at 30° C. The remaining oil was dissolved in chloroform (50 mL) and extracted with 5% aqueous citric acid (20 mL). The organic phase was dried over magnesium sulfate, filtered, and the solvent evaporated. A faint yellow oil was isolated (5.7 g). NMR spectra indicated that only about one third of the anhydride had been hydrolyzed. The crude material was redissolved in dioxane (20 mL) and water (10 mL). This mixture was stirred at 45° C. for 32 h. The solvents were evaporated in vacuo. NMR indicated that the hydrolysis of the anhydride was complete. The product was suspended in ethyl acetate (2 mL) and applied to a 25×4.5 cm column of silica gel 60 (150 g) equilibrated with hexane-ethyl acetate-acetic acid (100:50:1, v/v). The column was then eluted with the same solvent mixture. Fractions of 40 mL were collected at about 5 mL/min. Pure product was collected in fractions 16-21: (1.95 g, colorless oil): $^1$H-NMR (CDCl$_3$): δ 8.0 (m, 4H, Aromatic H), 7.38-7.60 (m, 6H, Aromatic H), 3.89 (m, 1H, CH—S), 3.0-3.3 (m, 2H, CH$_2$S), 2.34 (t, J=7.1 Hz, 2H, CH$_2$C(O)), 1.1-2.2 (m, 8H, CH$_2$); $^{13}$C-NMR (CDCl$_3$): δ 191.71, 191.46, 179.72, 136.98, 136.92, 133.29, 128.51, 127.25, 127.14, 43.60, 34.98, 34.59, 33.76, 26.43, 26.19, 24.29; TLC (hexane-ethyl acetate-acetic acid, 100:50:1, v/v), Rf=0.30; IR (neat): 2937, 1710, 1704, 1662, 1667, 1655, 1448, 1207, 1175, 911, 773, 757, 733, 648, 688 cm$^{-1}$.

Procedure 2: 6,8-Bismercaptooctanoic acid was acylated with 1.2 eq. of the appropriate carboxylic acid which had been pre-activated with CDI (1.2eq.) in DCM in the presence of triethylamine (1.2eq.). The products were purified by column chromatography on silica gel as described above.

Compound (K) was isolated during chromatography, as a side-product during the synthesis of compound (D).

EXAMPLE 3

General Procedure for Thioacetal Compounds (M), (N), (O), (P) and (Q)

The thioacetal compounds (M)-(Q) were synthesized by adapting the general procedures described in J. Am. Chem. Soc. 1993, 115, 3458 and J. Org. Chem. 1975, 40, 231:

To 6,8-bismercaptooctanoic acid (1eq.) in DCM under a nitrogen atmosphere, was added the appropriate aldehyde or ketone (1eq.). The mixture was stirred at room temperature for 1 h and cooled to −25° C. BF$_3$ etherate (1eq.) was added, and the reaction was allowed to warm to room temperature. After evaporation of the solvent, the products were purified either by crystallization or by chromatography on silica gel with ethyl acetate:hexane (1:2) as the eluent.

EXAMPLE 4

General Procedure for Bis-Alkylated Compounds (S), (T), (U), (V), (W), (X), (BB) and (II)

To 6,8-Bismercaptooctanoic acid (1eq.) in THF under a nitrogen atmosphere, the appropriate benzyl bromide, the phenethyl bromide or the alkyl bromide (2eq.) was added. Freshly prepared sodium ethoxide (3eq.) in absolute ethanol was added dropwise, with stirring over 10 min. The reaction mixture was then refluxed for 5.5 h and cooled to room temperature. After dilution with water, the solution was cooled in ice and acidified with 2N HCl to pH=2. The product was extracted with chloroform (×3), and the combined organic extracts were washed with water (×1), saturated aq. NaCl (×1), and dried (MgSO$_4$). Evaporation of the solvent gave the crude product which was crystallized from benzene and hexane or purified by column chromatography on silica gel with 1-3% methanol in DCM.

EXAMPLE 5

Synthesis of Compound (B)

Compound (B) was synthesized using a method adapted from Org. Lett. 2007, 6, 3687: 6,8-Bismercaptooctanoic acid (1eq.) and ferrocenemethanol (2.1eq.) in DCM were treated with trifluoroacetic acid (6.5eq.) at room temperature for 1 h. The solvent was removed, and the crude product was purified by using column chromatography on silica gel (hexane:ethyl acetate 2:1).

EXAMPLE 6

Synthesis of (Intermediate) Compound (J)

6,8-Bismercaptooctanoic acid (1.04 g, 5.0 mmol) was dissolved in trifluoroacetic acid (10 mL), under nitrogen. To this stirred solution, triphenylmethanol (1.30 g, 5.0 mmol) was added in small portions. The solution was stirred for 15 min and evaporated by using vacuum (2 mm at 10° C.). The resulting residue was dissolved in fresh trifluoroacetic acid (7 mL) and was stirred for 10 min. The solvent was removed under vacuum, and any remaining trifluoroacetic acid was removed by azeotroping with dry benzene (3×2 mL). TLC analysis of the residual viscous syrup ($CHCl_3$:$CH_3OH$:$CH_3COOH$, 100:10:1) revealed three spots with Rf values of 0.42, 0.47 and 0.54. The major spot had a Rf value of 0.47. The crude material was dissolved in chloroform (1 mL) and applied to a column (36×3.2 cm) which had been pressure-packed with silica gel (140 g), in $CHCl_3$:$CH_3OH$:$CH_3COOH$, 100:5:1. It is important that the column be packed very well and at least 100 g of silica be used for every gram of the reduced lipoic acid starting material. The column was initially eluted with the initial solvent mixture (100 mL). The column was then eluted with $CHCl_3$:$CH_3OH$:$CH_3COOH$ (100:7:1). Fractions of 20 mL were collected at 2 mL/min. Reasonably pure product was collected in fractions 10-16 to yield 1.44 g. This 6-mercapto-8-tritylmercaptooctanoic acid was used to synthesize compounds (Y), (Z) and (AA).

EXAMPLE 7

General Procedure for Compounds (Y) and (Z)

Syntheses of compounds (Y) and (Z) can be exemplified by the following general procedure for the synthesis of 6-ethylmercapto-8-tritylmercaptooctanoic acid, compound (Z): Compound (J) (1.09 g, 2.4 mmol) was dissolved in absolute ethanol (40 mL), and ethyl bromide (0.38 g, 3.0 mmol) was added. The stirred solution was placed under an atmosphere of nitrogen, and a solution of sodium ethoxide (10 mmol) in absolute ethanol (10 mL) was added over 5 min (this solution was freshly prepared by reacting sodium metal (0.23 g) with the ethanol). The solution was stirred at room temperature for 20 min. It was then heated under gentle reflux for 6 h (bath temp. 95° C.). A white solid was seen precipitating during this time. The mixture was cooled to room temperature, and the ethanol was evaporated in vacuo (1 mm at 10° C.). The residue was suspended in water (40 mL). The pH was adjusted to about 2 (pH paper) with 2M hydrochloric acid. The mixture was extracted with ethyl acetate (3×25 mL). The combined extracts were washed with saturated aq. NaCl (20 mL) and dried over magnesium sulfate. The solvent was evaporated to yield a yellow viscous oil weighing 1.14 g. The crude material in chloroform (2 mL) was applied to a column (25×3.2 cm) packed with silica gel of (90 g) in $CHCl_3$—$CH_3OH$—$CH_3COOH$, 250:10:1. Elution with this solvent yielded 0.85 g (74.5%) of a yellow syrup.

EXAMPLE 8

Synthesis of Compound (AA)

Compound (J) (6-Mercapto-8-trityl-bismercaptooctanoic acid) (1.36 g, 3.0 mmol) was dissolved in absolute ethanol (50 mL), and bromoacetic acid (0.63 g, 4.5 mmol) was added. The colorless solution was treated with a solution of sodium ethoxide (12 mmol) in absolute ethanol (10 mL) (this solution was freshly prepared by reacting sodium metal (0.28 g) with ethanol). A white solid formed upon addition. The mixture was stirred at room temperature for 30 min and then under gentle reflux for 7 hr (bath temperature 95° C.). The mixture was cooled to room temperature, and the solvent was evaporated under vacuum at room temperature to yield a pale yellow solid. The solid was dissolved in water (50 mL). The pH was adjusted to about 2 with 2M hydrochloric acid. A slightly yellow precipitate formed. The mixture was extracted with ethyl acetate (4×25 mL). The combined extracts were washed with saturated brine (20 mL). The solution was dried over magnesium sulfate, filtered and the solvent evaporated to yield a pale yellow viscous oil (1.59 g). TLC (Silica gel, 100:10:1 $CHCl_3$—$CH_3OH$—$CH_3COOH$) showed a major spot with Rf=0.42. The crude material was dissolved in chloroform (2 mL) and applied to a column (24×3.2 cm) that had been pressure-packed with silica gel (90 g) in $CHCl_3$—$CH_3OH$—$CH_3COOH$ (100:5:1). The column was then eluted with $CHCl_3$:$CH_3OH$:$CH_3COOH$ (100:10:1). Fractions (20 mL) were collected at 2 mL/min. The product was collected in fractions 14-20 to yield a colorless oil, 1.32 g (75% after correcting for residual acetic acid).

EXAMPLE 9

General Procedure for Compounds (G), (H) and (L)

The synthesis of compounds (G) and (H) can be exemplified by the following general procedure for 6-ethylmercapto-8-mercaptooctanoic acid (compound (H)): 6-Ethylmercapto-8-trityl-bismercaptooctanoic acid (0.85 g. 1.78 mmol) was dissolved in trifluoroacetic acid (10 mL). A deep yellow solution resulted. Triethylsilane (0.42 g, 0.58 mL, 3.6 mmol,) was added in one portion. A white solid was seen precipitating. The mixture was left at room temperature with occasional swirling for 10 min. The solid was removed by filtration and washed with trifluoroacetic acid (2×2 mL). The combined filtrates were evaporated to dryness in vacuo at room temperature and then azeotroped with benzene (2 mL) to yield an oil (0.49 g). TLC (silica gel, $CHCl_3$—$CH_3OH$—$CH_3COOH$ (100:5:1)) showed two spots with Rf=0.82 (triphenylmethane) and 0.35 (product). The crude material was added onto a column (22×2.3 cm) packed with silica gel (40 g) in $CHCl_3$—$CH_3OH$—$CH_3COOH$ (100:5:1). The column was eluted with this solvent to yield the product as a faint tan syrup: 0.33 g (78%). The product was stored in the dark, under nitrogen or argon, at −20° C.

Similarly, compound (G) was synthesized from compound (Y). Compound (L) was synthesized by a similar three-step procedure as used for compounds (H) and (G).

EXAMPLE 10

Synthesis of Compound (I)

Compound (AA), (6-Carboxymethylenemercapto-8-trityl-bismercaptooctanoic acid), was dissolved in trifluoroacetic acid (12 mL). Triethylsilane (0.53 g, 0.73 mL, 4.6 mmol) was added in one portion. The bright yellow solution became colorless, and a white solid precipitated. The mixture was left at room temperature with occasional swirling for 10 min and was filtered. The solid was washed with trifluoroacetic acid (2×3 mL). The combined filtrates were evaporated to dryness under vacuum at room temperature and azeotroped with benzene (2 mL) to give a faint brown oil (0.74 g). The crude material was dissolved in chloroform (1 mL) and added to a column (28×2.3 cm) packed with silica gel (40 g) in $CHCl_3$—$CH_3OH$—$CH_3COOH$ (100:5:1). The column was eluted with $CHCl_3$—$CH_3OH$—$CH_3COOH$ (100:7:1) to yield a viscous colorless syrup: 0.54 g (82%). The product should be stored in the dark, preferably under nitrogen, at −20° C. TLC: Rf=0.35 (100:7:1 $CHCl_3$—$CH_3OH$—$CH_3COOH$).

EXAMPLE 11

General Procedure for Compounds (CC), (DD), (EE), (FF) and (HH)

Compounds (CC), (DD), (EE), (FF) and (HH) were synthesized by using the above described procedures. Compound (J) was alkylated with bromoacetamide. The trityl protecting group was removed as described above to yield 6-acetamido-8-mercapto-6,8-bismercaptooctanoic acid. This intermediate was then alkylated with the appropriate alkyl bromides or benzyl bromide (for compound (HH)) in the presence of sodium ethoxide in refluxing ethanol as described previously.

EXAMPLE 12

Synthesis of Compound MM
(6-ethyl-8-phenyl-6,8-bismercaptooctanoic acid)

Cuprous iodide (12 mg) and anhydrous potassium carbonate (0.33 g, 2.4 mmol) were placed in a tube (15×2 cm) equipped with a magnetic stirring bar, and 6-ethylmercapto-8-mercapto octanoic acid (Compound (H)) (0.19 g, 0.8 mmol) in 2-methyl-2-butanol (2 mL) was added. The tube was closed with a septum cap and flushed with argon. Ethylene glycol (100 mg, 90 µL, 1.6 mmol) was added via a syringe followed by iodobenzene (164 mg, 90 µL, 0.8 mmol,). The tube was flushed again with argon, then sealed with parafilm and stirred at 95° C. for 38 h. The mixture was cooled to room temperature, and water (15 mL) was added. The pH of the suspension was adjusted to 2 with 2.0 M hydrochloric acid. The mixture was extracted with chloroform (3×10 mL). The combined extracts were dried over magnesium sulfate and filtered, and the solvent was evaporated to yield a yellow oil weighing 0.25 g. TLC ($CHCl_3$—$CH_3OH$—HOAc 100:10:1) and showing a major spot with Rf=0.45, a minor spot with Rf=0.39 and several minor spots. The crude product in chloroform (0.5 mL) was applied to a column (12×2.2 cm) with silica gel 60 (20 g) packed in $CHCl_3$—$CH_3OH$—HOAc (100:5:1). The column was eluted with $CHCl_3$—$CH_3OH$—HOAc (100:10:1). Fractions of 4-5 mL were collected at a flow rate of 0.5 mL/min. The product was collected in fractions 7-10: colorless oil weighing 140 mg. TLC Rf=0.45 (silica gel; $CHCl_3$—$CH_3OH$—HOAc, 100:10:1); $^1$H-NMR ($CDCl_3$): δ 7.1-7.4 (m, 5H), 3.08 (td, 2H), 2.6-2.8 (m, 1H), 2.48 (q, 2H), 2.35 (t, 2H), 1.3-1.9 (m, 8H), 1.22 (t, 3H); MS (ESI (−)): 311 (M-1).

EXAMPLE 13

Synthesis of Disulfide Compound (LL)

6,8-Bismercaptooctanoic acid (1.18 g, 5.67 mmol) in DCM (15 mL) and aldrithiol (5.0 g, 22.7 mmol, 4eq.) were treated with a catalytic amount of glacial acetic acid (32.5 uL, 2.5 mol %). The reaction was stirred at room temperature, under $N_2$, overnight. The solvent was evaporated under reduced pressure, and the crude product was purified by column chromatography on silica gel (80 g) with a solvent gradient of hexane to 50% ethyl acetate in hexane. MS: 425 (M-1).

EXAMPLE 14

Synthesis of Disulfide Compound (JJ)

The bispyridyl-6,8-dithiooctanoic acid disulfide (1eq.) obtained from above was dissolved in DCM, and benzyl mercaptan (2.5eq.) was added. The reaction was initiated by adding a catalytic amount of acetic acid (2.5 mol %). After stirring overnight at room temperature, the solvent was evaporated, and the crude product was purified by column chromatography on silica gel, with a solvent gradient of hexane to 50% ethyl acetate in hexane to elute the product. MS: 451 (M-1).

EXAMPLE 15

Synthesis of Compound (KK)

Aldrithiol (5.0 g, 22.6 mmol) in methanol (50 mL) was treated with acetic acid (33 uL, 0.565 mmol, cat.), and thiophenol (2.309 mL, 22.6 mmol, 1eq.) was added. The mixture was stirred at room temperature for 24 h. The solvent was evaporated under reduced pressure, and the crude compound was purified by column chromatography on silica gel (50 g), with hexane to 2% ethyl acetate in hexane as the eluent gradient: pale-yellow oil, 2.413 g (48.6%). This compound (500 mg, 2.279 mmol) was reacted with Compound (L) (237.39 mg, 1.14 mmol, 1eq.) in methanol (10 mL), with acetic acid (3.5 uL, 0.057 mmol, cat.). The reaction was stirred at room temperature for 24 h. The solvent was evaporated, and the compound was purified by preparative thin-layer chromatography on silica gel with 10% ethyl acetate in hexane as the developing solvent: pale yellow oil, 38 mg (9%), TLC (silica gel), Rf=0.18; MS (ESI (−)): 423 (M-1).

EXAMPLE 16

Synthesis of Compound (R)

Compound (R) was synthesized using a combination of the mono S-alkylation procedure of Example 9 and the thioacetal formation of Example 3.

Testing

Three human tumor cells were used in this investigation, and they were human H460 NSCLC, human melanoma A2058 and human adenocarcinoma HT1080 cell lines. Cells were originally obtained from American Type Cell Culture (ATCC) and have been used for experiments at passages below 30. All tumor cells were maintained at 37° C. in a humidified 5% $CO_2$ atmosphere in T75 tissue culture flasks containing 25 mL of Roswell Park Memorial Institute (RPMI) 1640, with 10% fetal bovine serum (FBS) and 2 mM L-glutamine. The tumor cells were split at a ratio of 1:10 every 4-5 days by trypsinization and resuspended in fresh medium in a new flask. Cells were harvested for experiments at 70-90% confluency.

The culture media used for all cell lines in this study was Roswell Park Memorial Institute (RPMI) 1640, with 10% fetal bovine serum (FBS), 2 mM L-glutamine, 100 IU/mL penicillin and 100 μg/ml streptomycin. The test compounds used were generally prepared at a concentration higher than 20 mM and tested at 1 mM in cultured media for precipitation. 1 mM is the highest tested concentration of the test compounds.

The anti-tumor activities of the test compounds were assessed by exposing the tumor cells to various concentrations of test compounds (or vehicle) or not treated with the test compounds or vehicle. The concentration ranges of the test compounds evaluated in this study were 0-1 mM. The duration of treatment of the tumor cells was 48 hours. Subsequent to treatment with the test articles, the number of viable tumor cells was determined, and the concentrations of the test agents that induced 50% of cell growth inhibition ($IC_{50}$) were derived and compared.

Cell Seeding for Experiments: To cells grown to 70-90% confluency, medium was removed and the cell monolayers were washed briefly by adding 5 mL of phosphate buffer saline (PBS) followed by aspiration. Trypsin-ethylenediaminetetraacetic acid (EDTA) (4 mL) was added to each flask, and the flask was placed in the tissue culture incubator for 5 minutes. Serum-containing medium (10 mL) was added to halt the enzymatic reactions, and cells were disaggregated by repeated resuspension with serological pipet. The cell-containing medium (20 μL) was added to 20 μL of 0.4% Trypan Blue solution, mixed, and 10 μL of this cell-containing mixture was placed in a chamber of a hemocytometer. The number of viable cells was determined by counting the number of viable cells (cells that excluded trypan blue) in the 4 corner squares of the hemocytometer chamber at 100× magnification. The volume of cells needed was determined by the following formula:

$$\text{Volume of cells needed} = \frac{\text{\# of cells wanted/mL}}{\text{\# of cells counted/mL}},$$

where # of cells counted/mL=average # of cells on hemocytometer×2 dilution factor×$10^4$.

The number of cells targeted for the study was 4×$10^3$ per well in 100 μL of medium. The actual number of cells were counted and seeded in the wells of a 96 well-plate. The cells were then incubated for ~24 hrs before they were used for testing of anti-tumor activities of the test compounds and vehicle. Cell monolayer was confluent or subconfluent for some cell lines at the day of the experiment.

Treatment with Test Compounds and Vehicle: On the day of testing, 5 μL of a specific concentration of the test compounds (or vehicle) were added to the wells. After exposure to the test articles (or vehicle) for 48 hours, the number of viable cells in the wells was determined (see next section), and the percent of cells relative to no treatment was calculated.

Determination of the Number of Viable Cells by the CellTiter Blue Assay: The number of viable cells was determined using the CellTiter Blue Assay in this study. Specifically, reagents were allowed to come to room temperature according to instructions from Promega, Inc. (Madison, Wis.). CellTiter Blue reagent was added with the 12-channel Eppendorf pipettor, 20 μL per well. The cells were then incubated at 37° C. for 1-4 hrs in cell culture incubator. Fluorescence intensity, which is proportional to the quantity of viable cells, was read at 530/590 nm using FLUOstar optima fluorescence plate reader (BMG technologies, Germany).

Calculations of $IC_{50}$ Values: Data from fluorescence readings were copied onto EXCEL spreadsheets, and cell growth relative to untreated cells was calculated, using the following equation:

% #cells relative to untreated=(mean luminescence at N/mean fluorescence untreated)×100% where N=concentration of the compound or vehicle.

The calculated values were imported into SigmaPlot, v9. A Four-Parameter Logistic Curve of the "mean relative cell growth as a function of the concentrations of the test compounds" was generated. The $IC_{50}$ values were determined from the curves. The R-squared value provided an indication of the degree of fitness of data to the curve. The $IC_{50}$ values for the tested compounds are set forth in Table 1 below.

TABLE 1

| Compound | $IC_{50}$ A2058 (melanoma) (μM) | $IC_{50}$ H460 (NSCLC) (μM) | $IC_{50}$ HT1080 (μM) |
|---|---|---|---|
| A | 183 ± 3 | 127 ± 11 | 80 ± 8 |
| E | 277 ± 9 | 234 ± 23 | 256 ± 19 |
| F | 51 ± 4 | 70 ± 13 | 68 ± 20 |
| H | 238 ± 2 | 282 ± 20 | 270 ± 4 |
| Q | 717 ± 11 | no data | no data |
| W | 125 ± 3 | 167 ± 42 | no data |
| X | 59 ± 4 | 64 ± 4 | 60 ± 18 |
| JJ | 206 ± 55 | 318 ± 20 | 133 ± 2 |
| KK | 483 ± 180 | 409 ± 69 | 212 ± 52 |
| LL | 745 ± 176 | 844 ± 176 | 737 ± 131 |
| MM | 346 ± 20 | 449 ± 1 | 421 ± 53 |

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A lipoic acid derivative selected from the group consisting of:

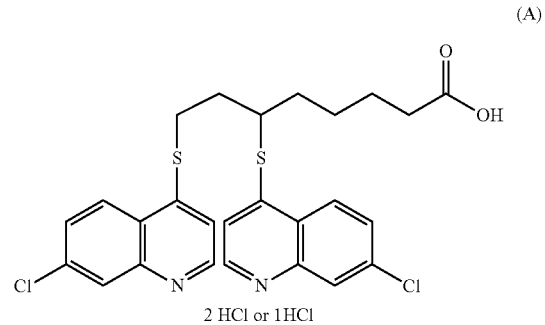

(A)

2 HCl or 1 HCl

-continued

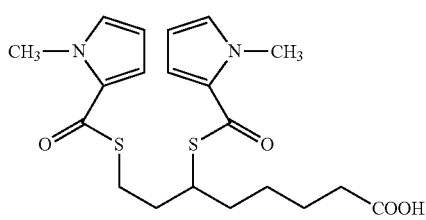
(C)

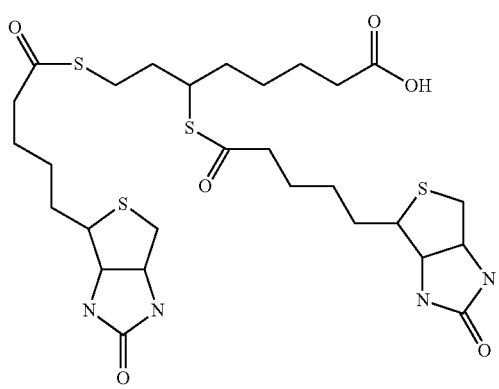
(D)

(E)

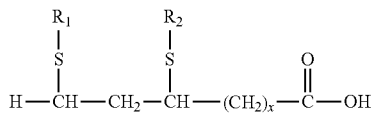

(F)

2. A pharmaceutical formulation comprising (a) a therapeutically effective amount of at least one lipoic acid derivative of claim 1 and (b) at least one pharmaceutically acceptable additive.

3. The pharmaceutical formulation of claim 2, wherein the at least one pharmaceutically acceptable additive is selected from the group consisting of solvents, diluents, surfactants, solubilizers, preservatives, buffers, and combinations thereof.

4. The pharmaceutical formulation of claim 2, wherein the at least one lipoic acid derivative is present in an amount to provide from about 0.001 mg/m² to about 10 g/m².

5. A method of treating lung cancer in a patient, comprising administering to a patient in need thereof a therapeutically effective amount of at least one lipoic acid derivative according to claim 1.

6. The method of claim 5, wherein the at least one lipoic acid derivative is in a pharmaceutical formulation further comprising at least one pharmaceutically acceptable additive.

7. A lipoic acid derivative having the following formula:

$$H-\overset{\underset{\displaystyle S}{|}}{\underset{\displaystyle |}{C}H}-CH_2-\overset{\underset{\displaystyle S}{|}}{\underset{\displaystyle |}{C}H}-(CH_2)_x-\overset{O}{\underset{\displaystyle \|}{C}}-OH$$

wherein $R_1$ and $R_2$ are independently a heteroaryl selected from the group consisting of benzothiazolyl, quinolinyl, or 7-chloroquinolinyl;

x is 0-16; or a salt thereof.

8. A lipoic acid derivative selected from the group consisting of:

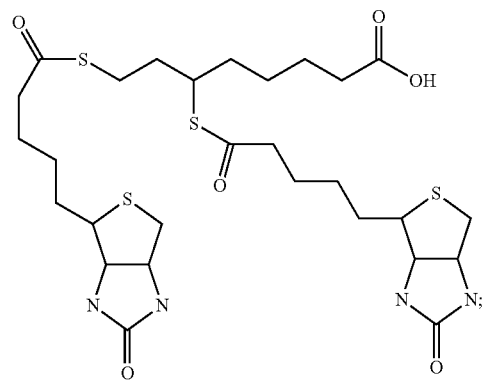

or a salt thereof.

9. A method of treating lung cancer in a patient, comprising administering to a patient in need thereof a therapeutically effective amount of at least one lipoic acid derivative of claim 7.

10. A method of treating melanoma or adenocarcinoma in a patient, comprising administering to a patient in need thereof a therapeutically effective amount of at least one lipoic acid derivative of claim 1.

11. A method of treating melanoma or adenocarcinoma in a patient, comprising administering to a patient in need thereof a therapeutically effective amount of at least one lipoic acid derivative of claim 7.

* * * * *